United States Patent

Tomiyama et al.

[11] Patent Number: 5,576,828
[45] Date of Patent: Nov. 19, 1996

[54] BONDING WIRE DETECTION METHOD

[75] Inventors: Hiromi Tomiyama, Musashimurayama; Satoru Nagai, Iruma, both of Japan

[73] Assignee: Kabushiki Kaisha Shinkawa, Tokyo, Japan

[21] Appl. No.: 525,284

[22] Filed: Sep. 8, 1995

[30] Foreign Application Priority Data

Sep. 9, 1994 [JP] Japan ..................................... 6-240790

[51] Int. Cl.$^6$ ............................. G01B 11/00; G01B 11/24
[52] U.S. Cl. ...................... 356/372; 356/376; 250/559.34
[58] Field of Search ................................... 356/372, 376, 356/375; 250/559.34

[56] References Cited

U.S. PATENT DOCUMENTS 4,942,618 7/1990 Sumi et al. ........................... 356/376
5,030,008 7/1991 Scott et al. ............................ 356/376
5,347,362 9/1994 Sugawara ............................. 356/372

Primary Examiner—F. L. Evans
Attorney, Agent, or Firm—Koda and Androlia

[57] ABSTRACT

The height of a wire bonded between a semiconductor chip and a lead frame being determined using an illumination from circularly arranged LED's installed in a low-angle illuminating device. The angle of the illumination is set at seven (7) to twelve (12) degrees, preferably at ten (10) degrees, with respect to a horizontal plane, and a focal depth of an optical device is set to be shallow, thus letting a dark area appear in the central portion of the wire at the focal point of the optical system.

3 Claims, 4 Drawing Sheets

FIG. 4
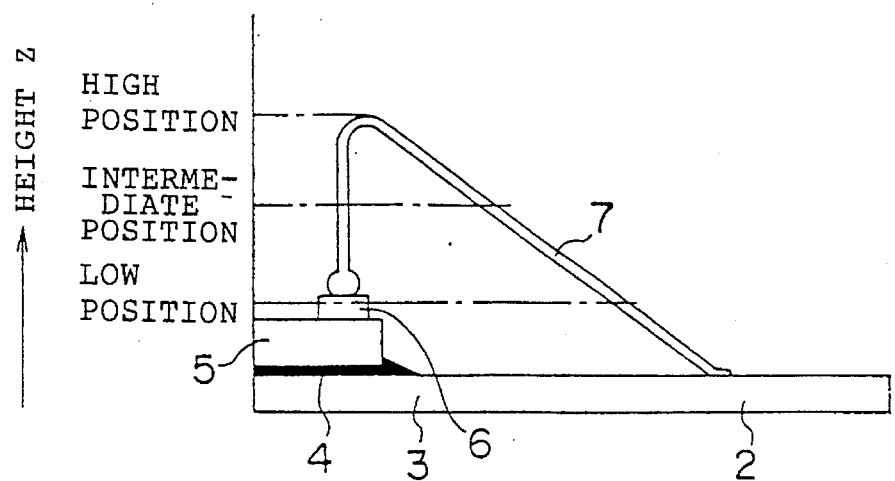
FIG. 5(a)   FIG. 5(b)   FIG. 5(c)
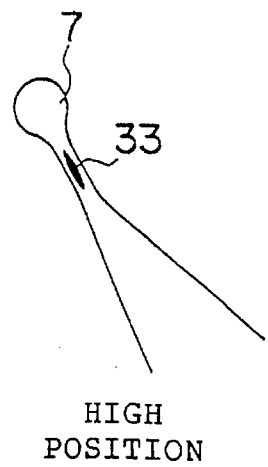
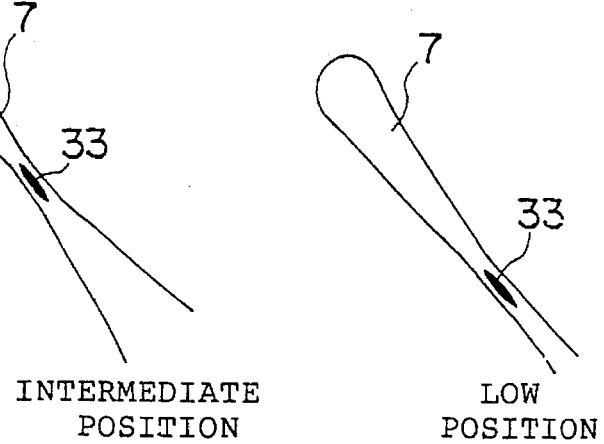
HIGH POSITION   INTERMEDIATE POSITION   LOW POSITION

BONDING WIRE DETECTION METHOD

BACKGROUND OF THE INVENTION

1. Field of the Invention

The present invention relates to a method for detecting wires bonded between the pads of semiconductor chips and the leads of lead frames.

2. Prior Art

The method described in U.S. Pat. No. 5,347,362, which corresponds to Japanese Patent Application Laid-Open (Kokai) No. 5-160233, is an example of one of the conventional methods for detecting bonded wires, particularly the height of the bonded wires. FIG. 6 shows the detection apparatus used in this method.

An exemplary workpiece 1 that is to be detected by this apparatus includes, as shown in FIG. 7, a semiconductor chip 5 installed on a lead frame 3 by a paste 4 which is an epoxy resin, etc., and wires 7 are bonded so as to connect the pads 6 of the semiconductor chip 5 to the leads 2 of the lead frame 3.

The detection apparatus of FIG. 6 includes an illuminating means 11 located above a detection stand 10 on which the workpiece 1 is placed for inspection. The illuminating means 11 is mounted to the lower part of an optical system 12, and an imaging device 14 such as a CCD (photoelectric transducer element) camera, etc. is mounted on the upper part of the optical system 12 with a diaphragm means 13 in between. The optical system 12 to which the illuminating means 11 and imaging device 14 are mounted is attached in a vertically movable fashion to a supporting block 16 which is installed on the surface of an XY table 15. The optical system 12 is moved up and down by a Z-axis motor 17.

As shown in FIGS. 8 and 9, the illuminating means 11 includes a high-angle illuminating device 22 and a low-angle illuminating device 24. In the illuminating device 22, LED's 21 are installed in the form of a ring around an opening 20a that is formed in an illumination retaining plate 20; and in the illuminating device 24, LED's 24 are also installed in the form of a ring so as to be positioned on the outside of the illuminating device 22. The LED's 21 and 24 of the high-angle illuminating device 22 and low-angle illuminating device 24 are oriented toward the optical axis of the optical system 12. The angle of inclination of the high-angle illuminating device 22 relative to a horizontal plane is set to be approximately 30 to 55 degrees, and the angle of inclination of the low-angle illuminating device 24 relative to the horizontal plane is set to be approximately 5 to 15 degrees.

When the height of a bonded wire is to be detected, the low-angle illuminating device 24 of the illuminating means 11 is controlled so that a part of its illumination is turned off as disclosed in the above-identified prior art, and the focal depth of the optical system 12 is set to be shallow via the diaphragm means 13.

More specifically, when wire detection is performed, the XY table 15 is moved horizontally so that the optical system 12 is, as shown in FIG. 7(a), positioned on a vertical line A which passes through the XY coordinates of one point on the wire 7 that is to be detected. Then, the Z-axis motor 17 is activated. The optical system 12 is raised and lowered by the motor 17 and focused at the detection point A0, resulting in that the image of the wire 7 appears as shown in FIG. 7(b). As seen from FIG. 7(b), the wire width H0 at the detection point A0 is imaged so as to appear with a minimum value, and the width of the image wire becomes larger and less distinct as the distance from the focal point A0 increases.

As disclosed in the prior art, there is a particular relationship between the blurring width (wire width) and the wire height Z as disclosed in the above-identified prior art; accordingly, if the relationship between the width and height beforehand were determined beforehand, the height of the bonded wire at an arbitrary point can easily be calculated (measured) from the wire width.

In the prior art described above, the wire height is measured based upon the imaged wire width using the in-focus wire image as a standard. In other words, the wire 7 is detected on the basis of the contrast between the wire 7 and the background. However, on a lead frame, the paste is squeezed out around the periphery of the semiconductor chip; and these squeezed out paste is imaged as bright areas by the imaging device. As a result, regions which are in the background of the wire and in which such squeezed-out paste is present cannot be contrasted with nor distinguished from the wire. In other words, a portion of the end part of the wire are not detected clearly.

SUMMARY OF THE INVENTION

The object of the present invention is to provide a bonding wire detection method which can be executed without being affected by the background.

The object of the present invention is accomplished by a unique manner taken in a wire detection method wherein wires bonded to pads of a semiconductor chip and leads of a lead frame are detected by illuminating a wire with a low-angle illuminating device of an illuminating means so as to take an image of the wire using an imaging device through an optical system, and the unique manner taken by the present invention is that the wire is illuminated by the low-angle illuminating device with LED's mounted in the illuminating device set at an angle of seven (7) to twelve (12) degrees with respect to a horizontal plane and with the focal depth of the optical system set to be shallow, thus creating a dark area in the central portion of the wire at the focal point of the optical system and detecting such a dark area for determining the wire height or the wire shape.

In the method of the present invention, the workpiece is illuminated by the LED's of the low-angle illuminating device, and the optical system is raised and lowered so that the optical system focuses the detection point of the wire. In this case, the illumination by the LED's of the low-angle illuminating device is set at an angle of seven (7) to twelve (12) degrees with respect to the horizontal plane, and in addition the focal depth of the optical system is set at a shallow depth. Accordingly, the reflection from the wire caused by illumination near the focal point shows that the edge portions of the wire are illuminated brightly while the central portion of the wire is dark. As a result, in the image of the wire obtained by the imaging device, a dark area appears in the center of the bright area in the vicinity of the focal point; and in the areas which are out of the focus, the image is indistinct and the dark area is canceled out by the bright areas, so that only bright areas remain. Accordingly, it can be recognized that the point at which the dark area appears is the focal point of the optical system, and the wire height is determined based upon such a focal point of the optical system.

BRIEF DESCRIPTION OF THE DRAWINGS

FIG. 4 is a front view showing the focal points on the wire;

FIGS. 5a)–5(c) show wire images with dark areas seen at different heights of a wire;

FIG. 7 shows the relationship between wire height and wire width of a sample obtained by a prior art detection method, wherein FIG. 7(a) is a front view of the sample, while

DETAILED DESCRIPTION OF THE INVENTION

One embodiment of the present invention will be described with reference to FIGS. 1 through 5. In this embodiment, detection is performed using the detection apparatus shown in FIGS. 6, 8 and 9.

Figure 6:
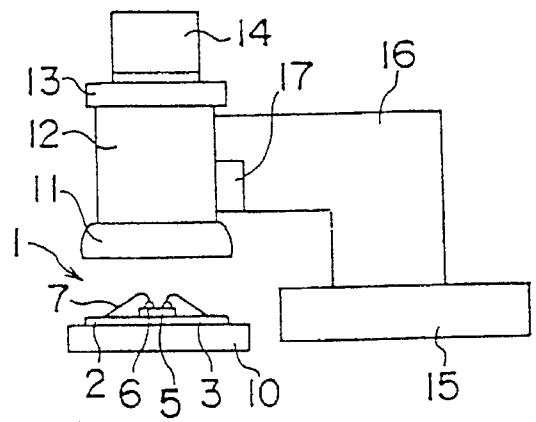
FIG. 6 is a schematic front view of a bonding wire height detection apparatus.
Figure 7A:
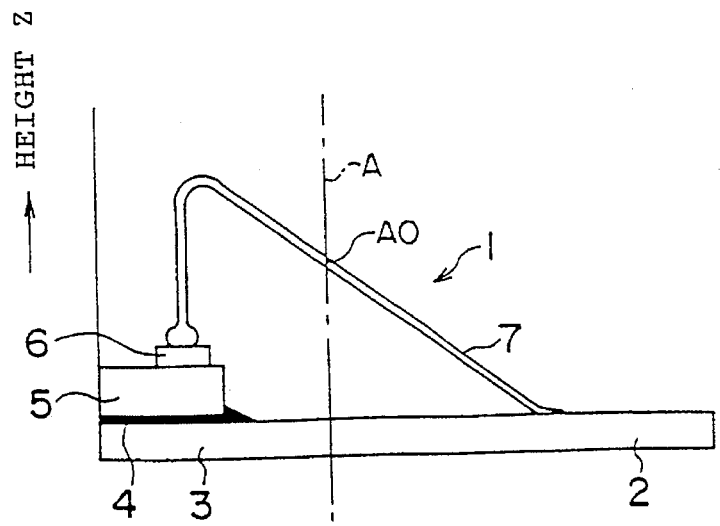
Figure 7B:
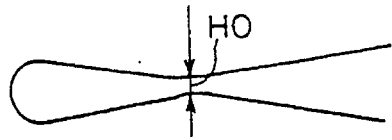
FIG. 7(b) shows the imaged width of the wire of the sample.
Figure 8:
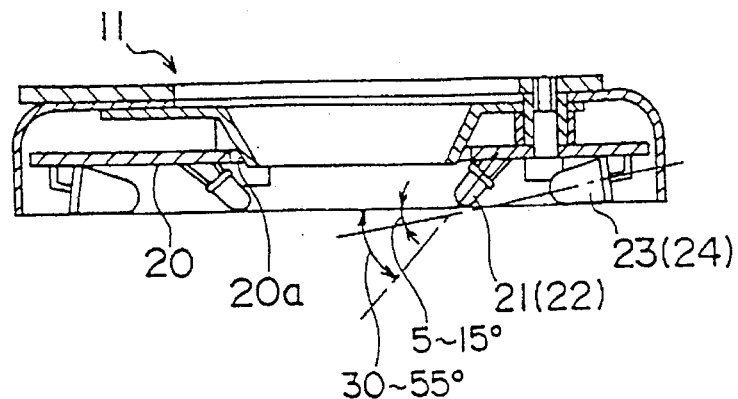
FIG. 8 is a sectional view of the illuminating means used in the detection apparatus of FIG. 6.
Figure 9:
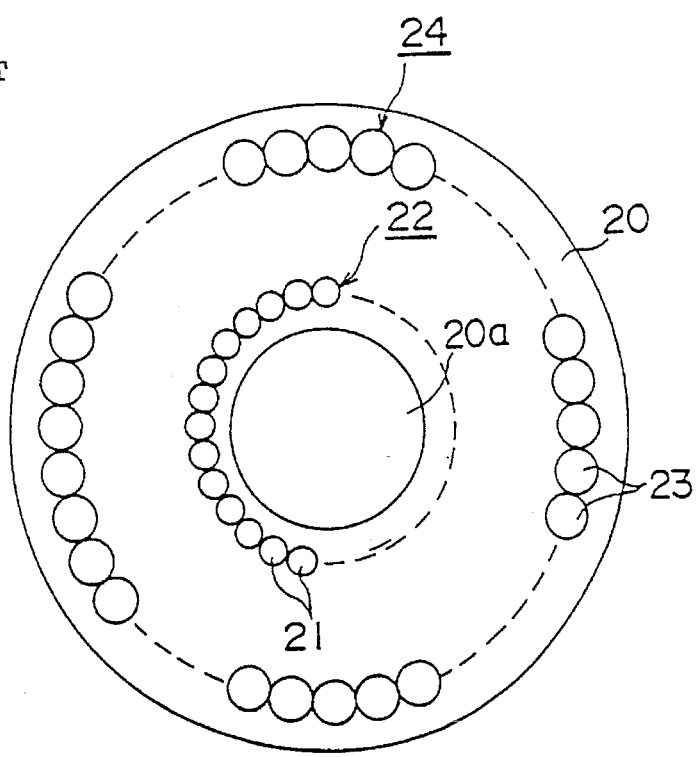
FIG. 9 shows the arrangement of the LED's used in the illuminating means of the prior art.

The inventors performed various intensive wire detection tests using the detection apparatus as shown in FIGS. 6, 8 and 9. The tests were conducted by turning on the low-angle illuminating device 24 of the illuminating means 11, turning off the high-angle illuminating device 22, and by setting the focal depth of the optical system 12 to be shallow by opening the diaphragm means 13. As a result, it was found that dark areas appear in the central portions of wires at the focal point of the optical system 12. The invention is derived from this finding.

Figure 1:
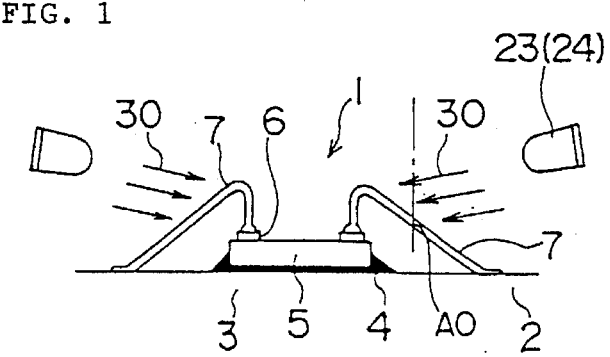
FIG. 1 illustrates the manner of illumination by the bonding wire detection method of the present invention.

More specifically, as shown in FIG. 1, the sample 1 is illuminated as shown by arrows 30 by the low-angle illuminating device 24, and the Z-axis motor 17 is actuated so that the optical system 12 is moved upward or downward, thus focusing the detection point A0 of the wire 7. In the present invention, the low-angle illuminating device 24 is set so that the illumination by the LED's mounted in the illuminating device 24 is performed at an angle of ten (10) degrees with respect to a horizontal plane. With this illumination angle, the reflection from the wire 7 that is caused by the illumination near the focal point A0 (detection point A0) of the wire appears such that the edge portions of the wire 7 are bright, and the central portion of the wire 7 is dark as shown in FIG. 2.

Figure 2:
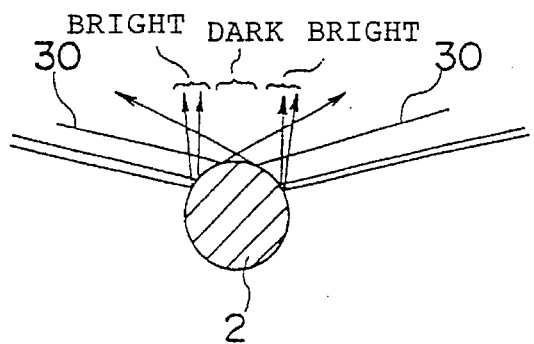
FIG. 2 shows the reflection of the illumination from a wire.
Figure 3:
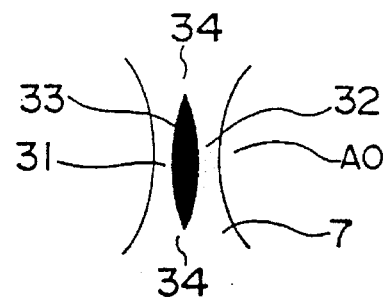
FIG. 3 illustrates a dark area on a wire at the focal point.

In other words, as seen from FIG. 3, the image obtained by the imaging device 14 under the situation described above shows that the vicinity area of the focal point A0 appears, corresponding to FIG. 2, as a dark area 33 with bright areas 31 and 32 on both sides thereof, and the image of the rest of the wire 7 which is not on focused appears indistinct with the dark area 33 faded out by the bright areas 31 and 32 at the edges of the wire, so that only a bright area 34 remains.

Accordingly, the point at which the dark area 33 appears is the focal point of the optical system 12, and such a focal point is obtained by the rotation of the Z-axis motor 17 that have moved the optical system 12 up and down. Thus, by determining the rotation of the Z-axis motor 17, the height of the wire at the focal point which is the detection point can be obtained.

Thus, by setting the optical system 12 at different heights on the wire by driving the Z-axis motor 17 so that the optical system 12 is moved up and down successively focused at a highest point H, an intermediate point I and a lowest point L as shown in FIG. 4, the dark area 33 will appear at each of these focal points at each height as shown in FIG. 5. Accordingly, the wire height and the XY coordinates at the location of the dark area 33 (i.e., at the focal point) are determined, and as a result, the wire shape can be determined from the XY coordinates of the focal points (three focal points in the above description).

As described above, the wire 7 is detected by setting the low-angle illuminating device 24 so that the angle of the illumination thereby is at ten (10) degrees relative to the horizontal plane and by setting the focal depth of the optical system 12 to be shallow by adjusting the diaphragm means 13. As a result, the dark area 33 will appear in the central portion of the wire 7 at the focal point, without being influenced by the background. The wire height and/or the wire shape can be constantly detected by detecting these dark areas 33.

Although the most desirable results are obtained with the angle of the illumination 30 of the low-angle illuminating device 24 set at ten (10) degrees, the angle may be set at any angle between seven (7) and twelve (12) degrees to obtain substantially the same results. In other words, by setting the LED's of the low-angle illuminating device so that the illuminating axis of each of the LED's is between seven (7) and twelve (12) degrees with respect to a horizontal plane, dark areas appear at the center of the illuminated circumference of the wire. However, if the angle is less than seven (7) degrees, the bright areas 31 and 32 become too small, while if the angle exceeds twelve (12) degrees, the dark area 33 becomes too small, thus enabling the detection of the dark areas 33.

As described above, according to the present invention, the illumination of the low-angle illuminating device is set at an angle between seven (7) and twelve (12) degrees with respect to the horizontal plane, and the focal depth of the optical system is set to be shallow. Thus, the dark areas appear in the central portions of a wire at the focal points of the optical system. Accordingly, the wire height and/or the wire shape are determined by detecting these dark areas without being influenced by the background.

We claim:

1. A bonding wire detection method in which a wire bonded to a pad of a semiconductor chip and a lead of a lead frame is detected by illuminating said wire with a low-angle illuminating device of an illuminating means so as to image said wire with an imaging device through an optical system, said method being characterized in that said wire is illuminated with an illumination of said low-angle illuminating device set at an angle between seven (7) to twelve (12) degrees with respect to a horizontal plane, and a focal depth of said optical system is set at a shallow depth, so that a dark area is created in a central portion of said wire at a focal point of said optical system, and a wire height and/or wire shape of said wire is detected by detecting this dark area.

2. A method for detecting a height of a wire bonded between a semiconductor chip and a lead frame by illuminating said wire with a light from an illuminating means which includes LED's disposed therein in a shape of circle and by taking an image of said wire with an imaging means by collecting reflections of said light from said wire through an optical means, wherein an illuminating axis of said LED's of said illuminating means is set at between seven (7) degrees and twelve (12) degrees with respect to a horizontal plane, and a focal depth of said optical means is set to be shallow, thus determining a height of a point of said wire by taking an image of a dark area which appears at a central portion of said wire.

3. A method according to claim 2, wherein said illuminating axis of said LED's is set at ten (10) degrees with respect to said horizontal plane.

* * * * *